United States Patent [19]

Braun et al.

[11] 4,175,423
[45] Nov. 27, 1979

[54] APPARATUS FOR DETERMINING THE PULSE REPETITION RATE OF A FLUIDIC OSCILLATOR THROUGH WHICH A TEST GAS IS FLOWING

[75] Inventors: Clarence Braun; Joseph E. Zupanick, both of Richardson, Tex.

[73] Assignee: Sun Oil Company (Delaware), Dallas, Tex.

[21] Appl. No.: 901,884

[22] Filed: May 1, 1978

[51] Int. Cl.$^2$ .......................... G01N 9/32; G01N 9/36
[52] U.S. Cl. ............................................. 73/30; 73/24
[58] Field of Search ..................... 73/30, 32 A, 23, 24; 137/835

[56] References Cited

U.S. PATENT DOCUMENTS

| | | | |
|---|---|---|---|
| 3,238,960 | 3/1966 | Hatch | 137/835 |
| 3,373,600 | 3/1968 | Taplin | 73/32 A |
| 3,554,004 | 1/1971 | Rauch et al. | 73/32 A X |
| 4,003,242 | 1/1977 | Houben et al. | 73/24 |
| 4,007,625 | 2/1977 | Houben et al. | 73/23 |
| 4,074,562 | 2/1978 | North | 73/32 A |

*Primary Examiner*—S. Clement Swisher
*Assistant Examiner*—Denis E. Corr
*Attorney, Agent, or Firm*—J. Edward Hess; Donald R. Johnson; James H. Phillips

[57] ABSTRACT

In order to determine the pulse repetition rate of a fluidic oscillator through which a test gas, whose density is to be determined, is flowing, the pressure pulses appearing at one outlet port of the oscillator is sensed with a pressure transducer. The pulses are integrated for a sample period such that, upon transfer or display, the accumulated count directly represents the average pulse repetition frequency during the sample. Means are provided, in a surge tank, for controlling the temperature and pressure of the test gas, and temperature and pressure transducers in communication with the sample fluid in the surge tank are each coupled to voltage-to-frequency converters which drive counters in order that the temperature and pressure of the test gas may also be displayed. An interface to a thermal printer allows the preservation of written records of prf, temperature, and pressure readings. An interface to a digital tape recorder permits magnetic recording of the data for subsequent processing.

6 Claims, 11 Drawing Figures

U.S. Patent  Nov. 27, 1979  Sheet 1 of 4  4,175,423
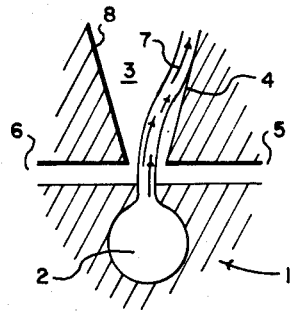
FIG. 1
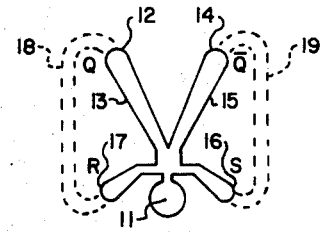
FIG. 2A
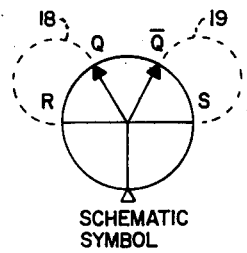
FIG. 2B
| R | S | Q | $\bar{Q}$ |
|---|---|---|---|
| X | 0 | 0 | X |
| 0 | 0 | 0 | X |
| 0 | X | X | 0 |
| 0 | 0 | X | 0 |
TRUTH TABLE
FIG. 2C
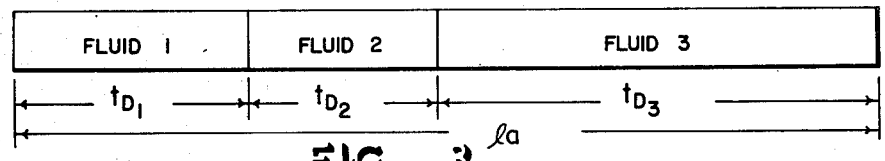
FIG. 3
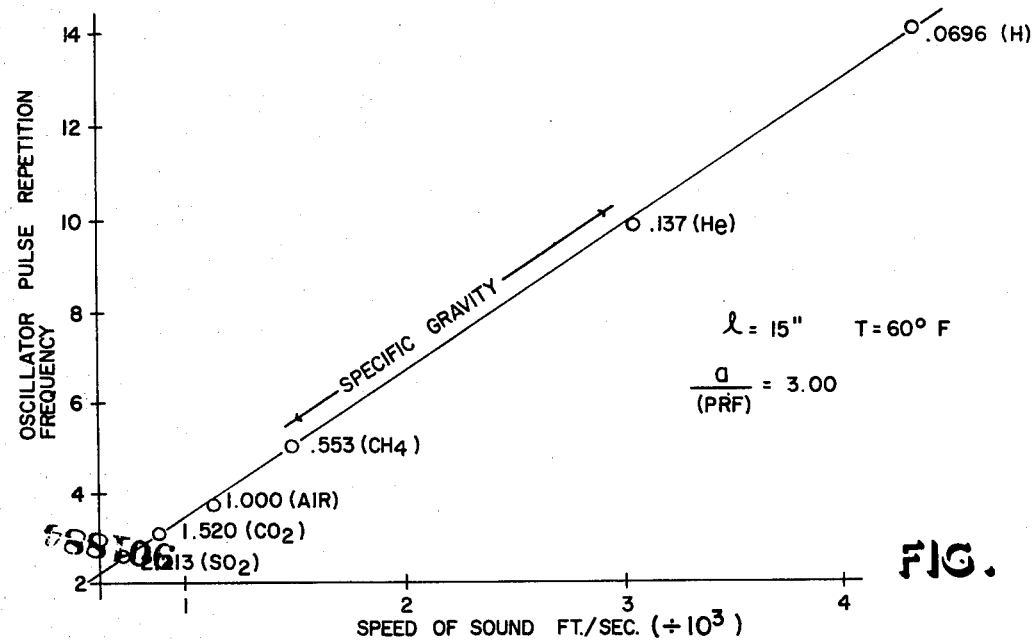
FIG. 4

APPARATUS FOR DETERMINING THE PULSE REPETITION RATE OF A FLUIDIC OSCILLATOR THROUGH WHICH A TEST GAS IS FLOWING

CROSS REFERENCE TO RELATED APPLICATIONS

This application contains subject matter related to copending applications Ser. No. 901,536, entitled "Means, Employing a Fluidic Oscillator, for Determining the Density of a Gas", and Ser. No. 901,535, entitled "Means, Employing a Fluidic Oscillator, for Determining the Constituent Gases of a Gas Mixture", each filed on even date herewith and assigned to the assignee hereof.

BACKGROUND OF THE INVENTION

This invention relates to the physical property measuring arts, and, more particularly, to apparatus for measuring the pulse repetition frequency of an astable oscillator in conjunction with the determination of the specific gravity of a gas.

There are many applications in which it is highly desirable to have means for easily and accurately determining the specific gravity of a gas. The term specific gravity defines the ratio of a density of any gas to the density of air where both gases are examined at standard conditions such as temperature and pressure. It has been determined, as described and claimed in the above mentioned related applications, that the pulse repetition frequency of an astable fluidic oscillator is related to the gas density and that the ratio of the pulse repetition frequency using the test gas as the working fluid and the pulse repetition frequency using air as the working fluid, given standard conditions, obtains the gas density.

In one specific application, the rapidly increasing cost of natural gas has inclined the industry to sell natural gas on the basis of its energy or caloric content. This approach requires a knowledge of the specific gravity of the natural gas as well as the constituents of the gas. The present invention finds particular use in such an application and comprises apparatus by which the pulse repetition frequency of a fluidic oscillator through which a test gas is passing is readily measured and displayed digitally along with the temperature and pressure of the test gas.

It is therefore a broad object of this invention to provide improved means for measuring the pulse repetition frequency of a fluidic oscillator along with the temperature and pressure of the motive gas.

It is another object of this invention to provide such apparatus which is simple and economical to fabricate.

It is yet another object of this invention to provide such apparatus which exhibits low power consumption and is therefore readily portable employing battery power.

SUMMARY OF THE INVENTION

Briefly, these and other objects of the invention are achieved by sensing the pressure pulses appearing at one output port of an astable fluidic multivibrator with a pressure transducer. The pulses are integrated for a sample period such that, upon transfer for display, the accumulated count directly represents the average pulse repetition frequency during the sample period. Temperature and pressure transducers in communication with the sample fluid in a surge tank are each coupled to voltage-to-frequency converters which drive similar counters in order that the temperature and pressure may also be displayed. In addition, an interface to a thermal printer allows the preservation of printed records in order that subsequent gas density determinations of a given sample may readily be made. CMOS logic is preferred to obtain readily portable, battery-powered operation.

DESCRIPTION OF THE DRAWINGS

The subject matter of the invention is particularly pointed out and claimed in the concluding portion of the specification. The invention, however, both as to organization and method of operation, may best be understood by reference to the following detailed description taken with reference to the accompanying drawing of which:

FIG. 1 is a simplified illustration of a fluidic bistable device;

FIG. 2A illustrates a practical fluidic bistable device along with its schematic representation;

FIG. 2B, and truth table;

FIG. 2C and also illustrates the manner in which feedback loops may be employed to convert the device for astable operation;

FIG. 3 illustrates a hypothetical representation of multiple gases in a feedback loop used in astable fluidic multivibrator;

FIG. 4 is a graph of the pulse repetition frequency of a fluidic oscillator through which various gases are flowing, plotted against the speed of sound;

DETAILED DESCRIPTION OF THE INVENTION

Figure 5:
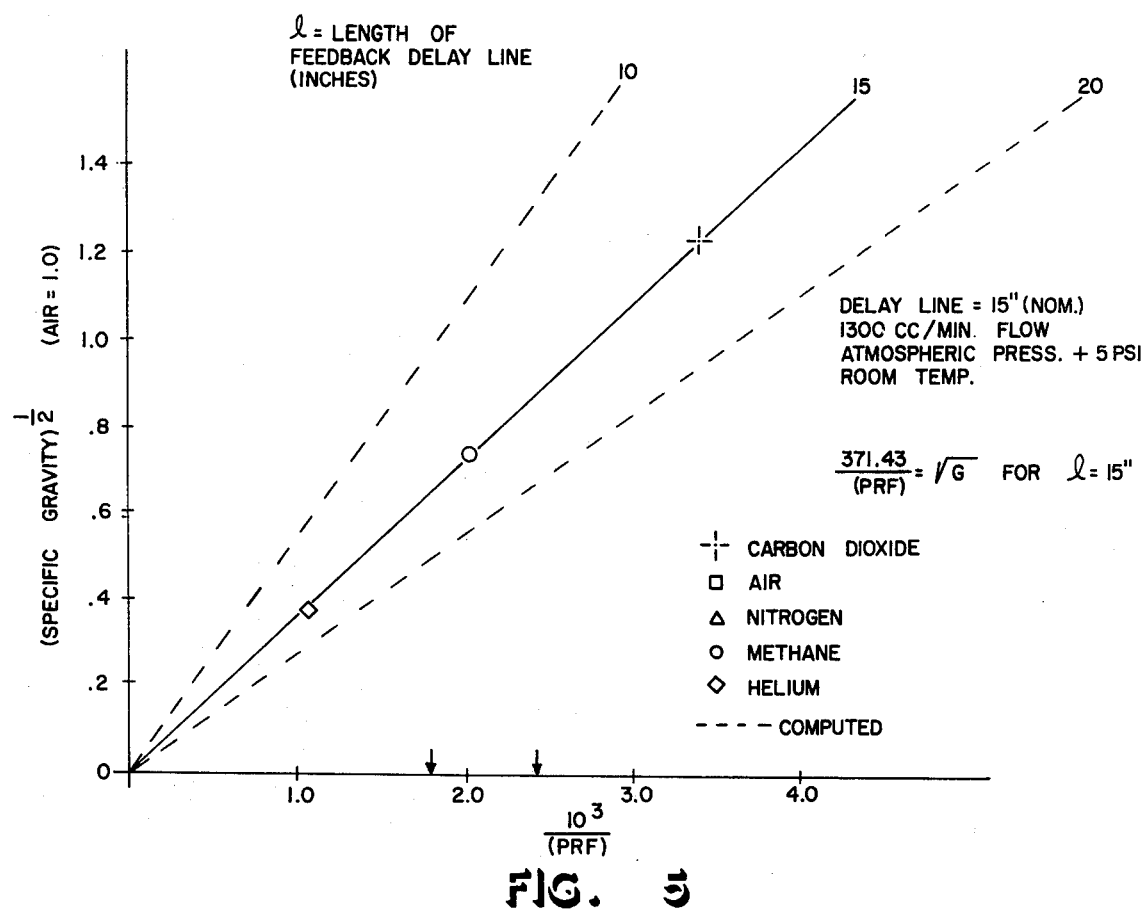
FIG. 5 is a graph of the square-root of specific gravity of various gases plotted against the reciprocal of the pulse-repetition-frequency of a specific fluidic oscillator through which the gases are flowing.

In order to fully appreciate the invention, it is useful to have a basic understanding of fluidic devices. Fluidics is an advanced control technology which has the unique capability to perform logic, signal amplification, and control functions using flowing fluid (gas or liquid) and no moving parts. Many different analog and digital fluidic devices are available; however, the present invention employs, as a fundamental component, a fluidic oscillator. Consider the primitive digital fluidic device 1 illustrated in FIG. 1. Fluid from a supply orifice 2 flows through and latches onto one wall 4 of an outlet passage 3. The fluid stream 7 remains latched onto the wall 4 because of the well-known Coanda effect. Control inputs 5 and 6, which are disposed, respectively, on the right and left sides and perpendicular to the fluid stream 7 in the region just beyond the supply orifice 2, are employed to switch the state of the fluidic device 1. More particularly, a momentary input fluid pulse passing through the control inlet 5 will impinge upon the fluid stream 7 and move it to the opposite wall 8 of the outlet passage 3. Thereupon, it will latch onto the wall 8 (because of the Coanda effect) and remain so latched until a control pulse is applied to the control input 6 to cause the stream 7 to switch back toward and latch onto the wall 4. Those skilled in the logic arts will immediately recognize that the bistable (flip-flop) function has been obtained.

A more practical fluidic bi-stable multivibrator is illustrated in FIG. 2 along with its schematic symbol in FIG. 2B and its logic truth table in FIG. 2C. Like numbers are employed to identify the same device elements in FIGS. 2A and 2B. Thus, a fluid stream from the supply port 11 of the bistable multivibrator 10 must either latch onto the outer wall 13 of Q output port 12 of on outer wall 15 of $\overline{Q}$ output port 14. Any position in between is unstable; the fluid stream must latch onto one or the other of the walls. As shown in the truth table, presence of a fluid pulse in reset control port 17 will cause the fluid stream to lock onto the wall 15 and thus appear at $\overline{Q}$ output port 14. Subsequent removal of the fluid stream from the reset control input port 17 will have no effect because the fluid stream is locked onto the wall 15 according to the aforementioned Coanda effect. A fluid pulse appearing at the set control input 16 will shift the fluid stream to lock onto the wall 13 and thus be present at the Q output port 12, and the subsequent removal of the input pulse from the set control input 16 causes no change in the state of the multivibrator.

Consider now the effect of adding the feedback loops 18 and 19 as shown as dashed elements in both FIGS. 2A and 2B. The Q output port 12 is coupled back to the reset control input 17, and the $\overline{Q}$ output port 14 is coupled back to the set input port 16. Assume as a starting condition that the fluid stream is latched onto the wall 13. The fluid stream thus flows through the Q output port 12, and for some delay time according to its length, through the feedback loop 18 to the reset control input 17. The appearance of a fluid pulse at the reset input 17 causes the fluid stream to shift and lock onto the wall 15 such that it commences flow out the $\overline{Q}$ output port 14 and, for a delay time which is a function of its length, through the feedback loop 19 to the set input port 16. The presence of the fluid pulse at the set input 16 causes the fluid stream to once again shift and latch onto the wall 13, and the cycle is repeated. Those skilled in the logic arts will immediately recognize the characteristics of the free running or astable multivibrator.

Thus, the operation of the fluidic oscillator is similar to an electronic astable multivibrator which has two outputs. Each output of the fluidic oscillator can have two stable states, a positive pressure or zero pressure, for example. However, the outputs are logically complementary. The feedback delay time $t_{Da}$ is the time required for a pressure pulse to travel the length of the feedback delay line 18. Similarly, the feedback delay time $t_{Db}$ is the time required for a pressure pulse to travel the length of the feedback delay line 19. These pressure pulses will travel along the feedback delay-line at the speed-of-sound of the resident gas. Therefore, the feedback delay-time $t_{Da}$ and $t_{Db}$ will be principally a function of the speed-of-sound for the particular fluid flowing in the feedback delay-lines and the respective lengths of $l_a$, and $l_b$, of lines 18 and 19.

Suppose that the delay-line 18 of length $l_a$ is filled with a fluid comprising three constituent gases as schematically represented in FIG. 3. Then, $$t_{Da} = t_{D1} + t_{D2} + t_{D3}$$

Equation A-1

The three fluids will have a speed-of-sound of $a_1$, $a_2$, and $a_3$, and their respective lengths will be $l_1$, $l_2$, and $l_3$. Let $$P_1 l_a = l_1$$

$$P_2 l_a = l_2$$

$$P_3 l_a = l_3$$

Where $P_1$, $P_2$ and $P_3$ are fractions of the total length such that $$P_1 + P_2 + P_3 = 1.0$$

Then, $$t_{D1} = l_1/a_1 = P_1 l_a/a_1$$

$$t_{D2} = l_2/a_2 = P_2 l_a/a_2$$

$$t_{D3} = l_3/a_3 = P_3 l_a/a_3$$

Substituting these last three expressions into equation A-1, the result is:

$$t_{Da} = (P_1 l_a/a_1) + (P_2 l_a/a_2) + (P_3 l_a/a_3)$$

or $$t_{Da}/l_a = (P_1/a_1) + (P_2/a_2) + (P_3/a_3) = 1/a_x$$

Equation A-2 where $a_x$ is the speed-of-sound in the exemplary fluid made up of three constituent gases.

In order to establish a relationship of the speed-of-sound "a" to the pulses generated by the fluidic oscillator (which will be referred to as the pulse-repetition-frequency) [prf], it can be stated that, for a perfect gas, $$a^2 = \frac{(32.17)(k)}{\rho}$$

where
  32.17 = dimensional constant = (lb)(ft)/(lb-force)(sec$^2$)
  k = fluid bulk modulus of elasticity—(lb-force)/(sq ft)
  $\rho$ = fluid density—(lb)/(cu ft)
  a = speed-of-sound—(ft)/(sec)
or $$a_x = K_1/\rho_x$$

(See for example, Perry, Chilton and Kirkpatrick, Perry's Chemical *Engineers Handbook,* Fourth Edition, Section 5-15.) It has been demonstrated experimentally with a fluidic oscillator that $$\sqrt{G} = \text{``}L\text{''}/(\text{prf}) = \sqrt{\rho_x}/\rho_{air}$$

Equation A-3

$$\sqrt{p_x} = "L" \sqrt{\rho_{air}}/(prf)_x = K_2/(prf)$$

Equation A-4 where G = the test gas specific gravity
where L ≈ feedback delay line length plus an amount which accounts for the switching time, determined experimentally as discussed below.
Combining equations A-3 and A-4, the result is obtained $$a_x = K_x(prf)_x$$

Equation A-5

Substituting Equation A-5 into A-2, the following expression relates the fluidic oscillator (prf) of the FIG. 3 constituent gases to the (prf) of the composite gas, ie.

$$\frac{1}{K_x(prf)_x} = \frac{P_1}{K_1(prf)_1} + \frac{P_2}{K_2(prf)_2} + \frac{P_3}{K_3(prf)_3}$$ Equation A-6

The K values in Equation A-6 were computed for a variety of constituent gases (for example, air, carbon dioxide, methane, helium, nitrogen, hydrogen, and sulfur dioxide) and for specific conditions of feedback delay-line of 15", a temperature 60° F. and gauge pressure of 5 psi, and was found to be a constant of three under these conditions, See FIG. 4. Therefore, Equation A-6 can be written, provided that the conditions are met, as:

$$\frac{1}{(prf)_x} = \frac{P_1}{(prf)_1} + \frac{P_2}{(prf)_2} + \frac{P_3}{(prf)_3}$$ Equation A-7

If it is not possible to assume that $$K_x = K_1 = K_2 = K_3$$

in Equation A-6, then the procedures may be modified as follows. The values of $K_1$, $K_2$, $K_3$, may be determined by experiment for the constituent gases. However, $K_x$ is an unknown because it is for the composite gas. Thus, first assume a value for $K_x$ on the basis of historical data or, more simply, first assume that all the K's are equal and solve for the P's as previously discussed. With this first iteration on the P's and the known values of $K_1$, $K_2$, $K_3$, a first estimate of the value of $K_x$ may be made to obtain a second set of P values. This iterative procedure can be continued until the difference between successive iterations is small and within the limits of the required accuracy. As a practical matter, a programmable hand calculator can readily be programmed to carry out the computations and display the results in a few seconds.

As previously stated, the reciprocal of the prf of a fluidic oscillator is proportional to the square root of the specific gravity, and this can be shown theoretically as will be set forth below. However, the theoretical result, which only considers the length of the feedback delay line, is somewhat in error because of the time delay during switching of the flowing stream. Thus:

$$t_{De} = t_{Dl} + t_{Ds}$$

Equation B-1

Where:
$t_{De}$ = Delay-time involved in switching from state "Q" to state "$\overline{Q}$" or visa-versa, experimentally determined.
$t_{Dl}$ = The delay-time while the pressure pulse travels along the feedback delay-line length.
$t_{Ds}$ = The delay-time required to switch the flow from one wall of the fluidic oscillator to the other.
For a specific configuration, the value of $t_{Dl}$ can be obtained analytically and the value of $t_{De}$ is known from experimental results. The switching delay time of $t_{Ds}$ is then simply: $t_{De} - t_{Dl}$. The pulse-repetition-frequency (prf)$_e$ determined from experimental data is defined as:

$$(prf)_e = 1.0/2t_{De}$$

Equation B-2

The pulse-repetition-frequency for the portion due only to the delay-line length l is:

$$(prf)_l = 1.0/2t_{Dl} = a/2l$$

Equation B-3 because $$t_{Dl} = l/a$$

Equation B-4 where
a = speed-of-sound in the fluid
l = physical length of the fluidic oscillator feedback delay-line
From, for example, the previously mentioned *Perry's Chemical Engineers Handbook*:

$$a = 32.17 \ (kRT/M)$$

Equation B-5 where:
32.17 = dimensional constant (lb.)(ft)/(lb-force)(sec²)
k = ratio of specific heats—dimensions
R = gas constant (1546)(ft)(lb-force)/(°R)(lb-mole)
M = molecular weight of the fluid (lb)/(lb-mole)
T = absolute temperature of the fluid (°F.+460)
For example, for air:
M = 29
T = 60° F. (assumed)
k = 1.4
a = 1117.26 (ft/sec)
Then, for l = 15" (1.25 feet) and using Equation B-3:

$$(prf)_l = \frac{1117.26}{2(1.25)} = 446.9 \text{ (pulses per second)}$$ Equation B-6

$$2t_{Dl} = \frac{1.0}{(prf)_l} = \frac{1.0}{446.9} = 02242 \text{ sec} \quad \text{Equation B-7}$$
$$(2.242 \text{ msec})$$

From experimental data, it is known that the actual (prf)$_e$ = 377 pulses per second for an l = 15 inches or $$2t_{De} = 1.0/377 = 0.002653 \text{ sec (2.653 msec)}$$

Equation B-8 from Equation B-1, $$2t_{D_s} = 2t_{D_e} - 2\ t_{D_l}$$
$$= 2.653 - 2.242 = .411 \text{ msec or}$$
$$t_{D_s} = .205 \text{ msec}$$

Thus, the time to switch flow for the exemplary fluidic oscillator is approximately 0.2 milliseconds. (15.5% of the total switching time)

It is now possible to define a new length l' which is the "effective length" of the fluidic oscillator feedback delay-line, where $$l' = \frac{a}{2(prf)_e} = \frac{1117.26}{2(377)} = 1.48 \text{ feet} \quad \text{Equation B-9}$$
$$l' = 17.78 \text{ inches}$$

Of course, it is assumed that the speed-of-sound complies with the perfect-gas law. This appears to be a valid assumption under these conditions, but experimental results can be used if the perfect-gas law proves to be insufficiently precise for a given purpose.

The previous analysis indicates a switching delay-time of about 0.2 msec, using air as the working fluid. The question arises, how is this switching time influenced by fluids other than air? From Equations A-3 and B-6:

$$(prf)_l = 446.8/\sqrt{G} = 1.0/2t_{D_l}$$

Equation B-10

$$(prf)_e = 378/\sqrt{G} = 1.0/2t_{D_e}$$

Equation B-11

Substituting Equations B-10 and B-11 into Equation B-1, $$2t_{D_s} = \sqrt{G}\left(\frac{1}{378} - \frac{1}{447}\right) \quad \text{Equation B-12}$$

$$t_{D_s} = \sqrt{G}\,(0.205) \text{ msec}$$

Equation B-13

Equation B-13 shows that the switching delay is proportional to the square root of specific gravity G for a fluid temperature of 60° F. and 5 psi gauge pressure.

Figure 6:
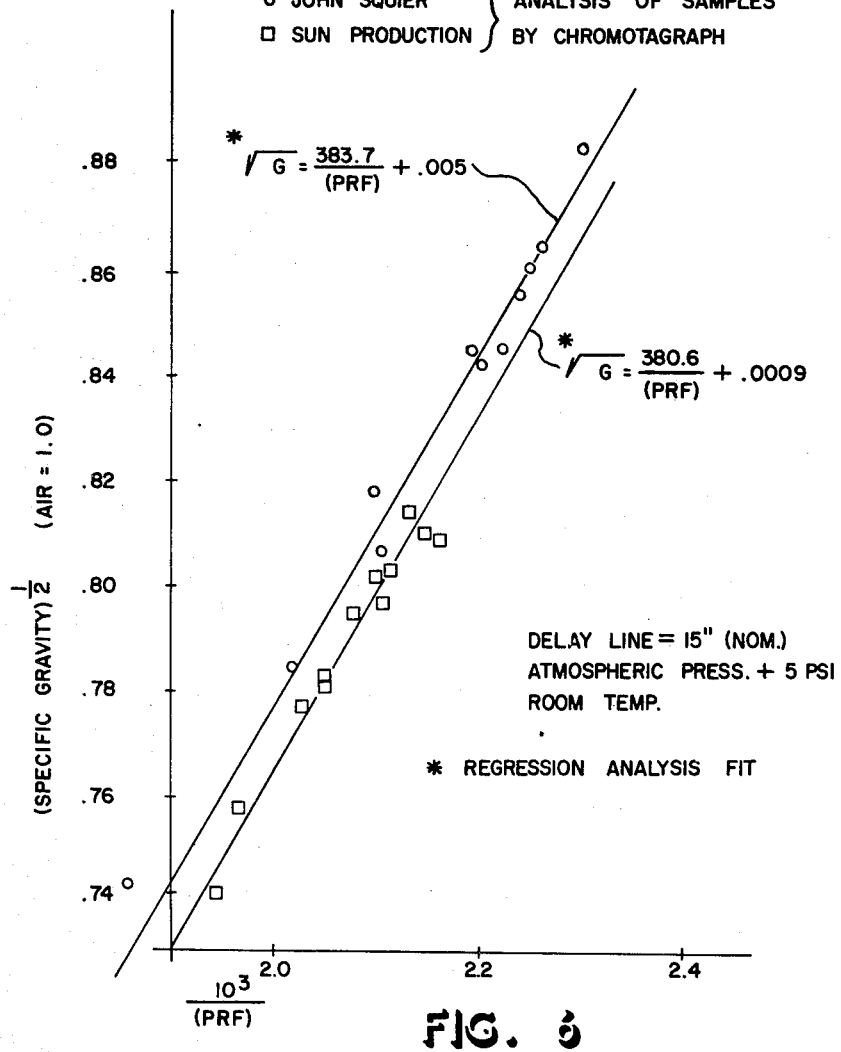
FIG. 6 is a graph illustrating experimental results of testing various natural gas field samples, similar to FIG. 5, but presented on an expanded scale.

As a practical matter, the prf is determined experimentally to develop a curve such as shown in FIG. 5 or the more expanded FIG. 6. With respect to FIG. 5, it may be noted that the relationship between the recipricol of the fluidic oscillator prf and the $\sqrt{G}$ is linear and this appears to be borne out by experimental results. Even if not linear, of course, the curve can be utilized in a practical sense. It should also be noted that in FIG. 5, a value of 371.4 is shown for "L", whereas a value of 378 is employed in the analysis. The difference results from using experimental data which became available later in time and from the fact that the value of 378 was computed on the basis of a linear regression analysis of this later data. As is practical, each individual fluidic oscillator may have a specific value of "L" best determined by experimental calibration.

Briefly then, in order to obtain the specific gravity of a gas, the sample fluid stream is allowed to expand to approximately 5 psi above atmospheric conditions and pass through the fluidic oscillator, and the prf of this gas sample is noted. Air is also passed through the same fluidic oscillator (or a similar unit) to determine the prf for air under the same conditions. The specific gravity of the gas sample is then simply the ratio of the square of the prf of the sample to the square of the prf of air. As a more practical expedient, the prf of the gas sample and the observed gas temperature and pressure may be employed to obtain the gas density by simply referring to a chart prepared in accordance with the foregoing.

The reciprocal of the pulse-repetition-frequency is plotted against the square root of specific gravity on FIG. 6 for two sets of field samples referred to as "John Squier" and "Sun Production". The value of "L" was obtained by performing a linear regression analysis on each set of data. The following results were obtained, see FIG. 6:

$$G = \frac{383.7}{(prf)} + .005$$
$$G = \frac{380.6}{(prf)} + .0009$$

The value of "L" from these two equations is

"L" = 383.7 and

"L" = 380.6

These two values of "L" differ by approximately 1%, but these specific results should not be construed to mean that this is representative of the capability for precision of the method. The early experimental apparatus used to obtain these results was very simple, a microphone and pulse counter with the fluidic oscillator operated at room temperature which was not closely controlled. The difference noted could result simply from an eight degree temperature difference. It should be noted that the range of values for natural gas in FIG. 6 are designated by the two "tic's" straddling the value 2.0 on the horizontal coordinate of FIG. 5, which then strongly suggests that the relationship in FIG. 5 is indeed linear.

The foregoing analysis provides a foundation for realizing means by which the percentage of each constituent gas in a composite gas sample, or a determination of the percentage of a gas sample which is inert. The pulse-repetition-frequency $(prf)x_{T_o}$ of the composite gas is observed by flowing the stream through an instrumented fluidic oscillator as previously discussed. Some heat is then added to the flowing gas sample, and a new $(prf)x_{T_1}$ at a new temperature $T_1$ is observed. This temperature $T_1$ is important and must be recorded. Still more heat is added and the prf and temperature are recorded each time an additional amount of heat is added, yielding:

$(prf)x_{T_2}$ at $T_2$
$(prf)x_{T_3}$ at $T_3$
$(prf)x_{T_4}$ at $T_4$

It is known from Equation A-7 that the pulse-repetition-frequency of the composite gas $[(prf)x_{T_o}]$ has the following relationship:

$$\frac{1}{(prf)x_{T_o}} = \frac{P_1}{(prf)1_{T_o}} + \frac{P_2}{(prf)2_{T_o}} + \frac{P_3}{(prf)3_{T_o}} + \ldots + \frac{P_n}{(prf)n_{T_o}} \quad \text{Equation C-1}$$

where:

(prf)$x_{T_o}$—is the oscillator pulse-repetition-frequency for the constituent gas methane ($CH_4$) at a pressure $P_o$ and a temperature $T_o$. This oscillator pulse-repetition-frequency (prf)$1_{T_o}$ is determined from FIG. 5 or an equivalent analytical expression.

$P_1$—is the unknown percentage of methane in the total volume of the sampled gas.

(prf)$2_{T_o}$—is the oscillator pulse-repetition-frequency for the constituent gas nitrogen ($N_2$) at a pressure $P_o$ and a temperature $T_o$. This oscillator pulse-repetition frequency (prf)$2_{T_o}$ is determined from FIG. 5 or an equivalent analytical expression.

$P_2$—is the unknown percentage of nitrogen in the total volume of the sampled gas and similarly for the other constituent gases which are known to be or assumed to be in the gas sample.

The following set of linear equations, where the P's are unknown, can then be written:

$$\frac{1}{(prf)x_{T_o}} = \frac{P_1}{(prf)1_{T_o}} + \frac{P_2}{(prf)2_{T_o}} + \frac{P_3}{(prf)3_{T_o}} + \ldots + \frac{P_n}{(prf)n_{T_o}}$$

$$\frac{1}{(prf)x_{T_1}} = \frac{P_1}{(prf)1_{T_1}} + \frac{P_2}{(prf)2_{T_1}} + \frac{P_3}{(prf)3_{T_1}} + \ldots + \frac{P_n}{(prf)n_{T_1}}$$

$$\vdots$$

$$\frac{1}{(prf)x_{T_n}} = \frac{P_1}{(prf)1_{T_n}} + \frac{P_2}{(prf)2_{T_n}} + \frac{P_3}{(prf)3_{T_n}} + \ldots + \frac{P_n}{(prf)n_{T_n}}$$

Equation family C-2

Figure 8:
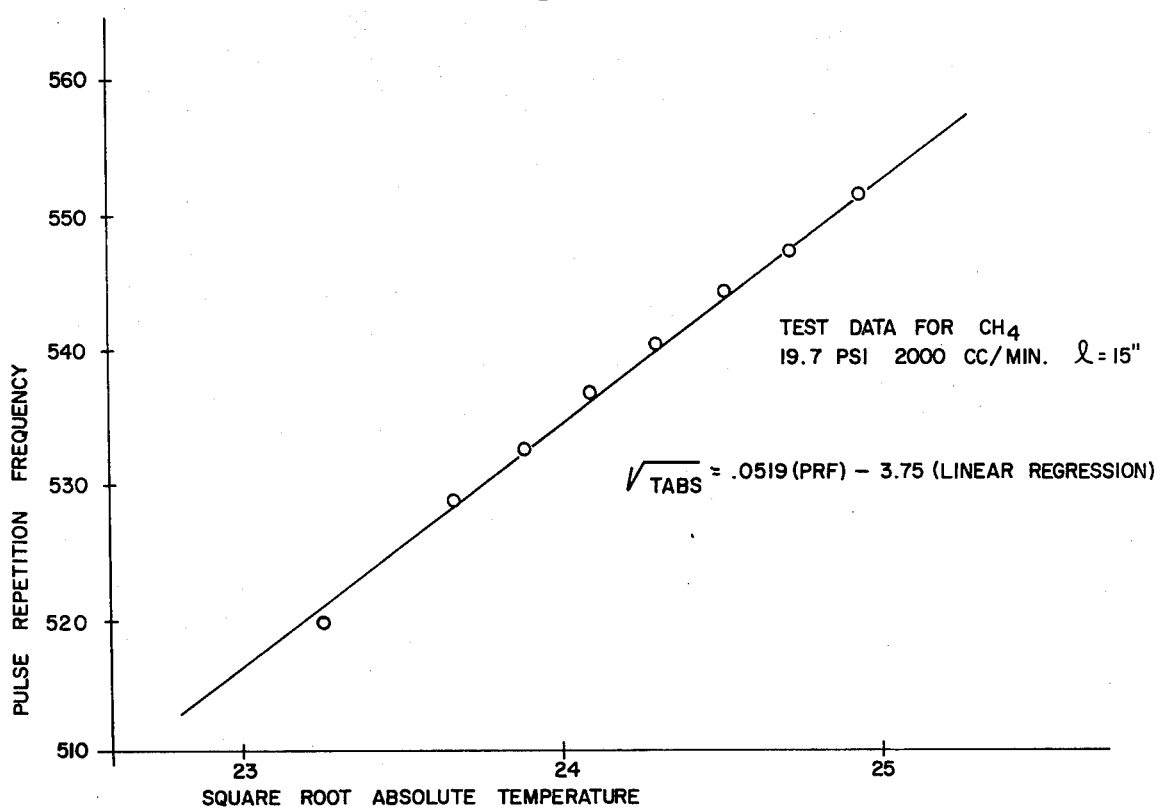
FIG. 8 is a graph similar to that presented in FIG. 7, but illustrating the corresponding characteristics of methane.
Figure 7:
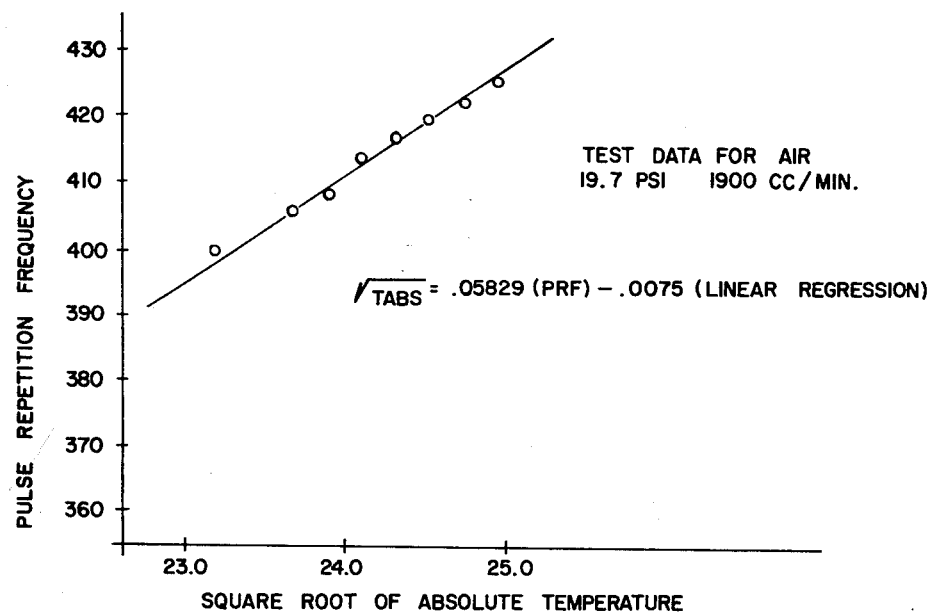
FIG. 7 is a graph illustrating the relationship of the pulse-repetition-frequency of a given fluidic astable oscillator for air under constant pressure, variable temperature conditions.

As an example, suppose it is desired to know the percentage of hydrocarbon gas and the percentage of inert gases nitrogen ($N_2$) and carbon dioxide ($CO_2$) in a composite gas sample. For purposes of this example, it will be assumed that the hydrocarbon gas is only methane ($CH_4$) and that the following observations were made from field measurements for the composite gas sample:

(prf)$x_{T_o}$ = 482.93 pulses per second
(prf)$x_{T_1}$ = 499.55 pulses per second
(prf)$x_{T_2}$ = 538.79 pulses per second From a derived expression of temperature in relation to frequency and experimental data prepared as discussed above, see FIGS. 7 and 8, the following form of expressions may be written for the three constituent gases methane, ($CH_4$), nitrogen ($N_2$), and carbon dioxide ($CO_2$), which were chosen for the example, $\sqrt{T_{abs}} = K(prf)$, for air at gauge pressure of 5 psi, feedback delay-length of 15" and room temperature, K = 0.05829.
Then:
for methane—$CH_4$
(prf)$1 = \sqrt{T_{abs}}/0.0485$ from which the following is derived:
(prf)$1_{T_o}$; (prf)$1_{T_1}$; (prf)$1_{T_2}$
for nitrogen—$N_2$
(prf)$2 = \sqrt{T_{abs}}/0.0583$ from which the following is derived:
(prf)$2_{T_o}$; (prf)$2_{T_1}$; (prf)$2_{T_2}$
for carbon dioxide—$CO_2$
(prf)$3 = \sqrt{T_{abs}}/0.0805$ from which the following is derived:
(prf)$3_{T_o}$; (prf)$3_{T_1}$; (prf)$3_{T_2}$ Using the above derived values and the values of (prf)$x_{T_o}$, (prf)$x_{T_1}$, and (prf)$x_{T_2}$ which have been obtained from field measurements, the following three linear equations can be written. (It may be noted that these equations have been multiplied through by 1000 to obtain manageable values.)

$$\frac{1000}{(prf)x_{T_o}} = 2.0707; \frac{1000}{(prf)x_{T_o}} = 2.0018 \text{ and } \frac{1000}{(prf)x_{T_2}} = 1.8560$$

$2.0707 = 2.12\ P_1 + 2.50\ P_2 + 3.53\ P_3$

Equation C-3

$2.0018 = 2.05\ P_1 + 2.45\ P_2 + 3.40\ P_3$

Equation C-4

$1.8560 = 1.90\ P_1 + 2.30\ P_2 + 3.15\ P_3$

Equation C-5

Thus, there are three unknowns and three equations which will permit solutions for $P_1$, $P_2$, and $P_3$. There is another governing equation and that is that $P_1 + P_3 + P_3 = 1.0$, that is, the sum of the percentages of the constituent gases must be equal to 100%. However, if three constituent gases, say $P_1$, $P_2$, $P_3$, are assumed and in actuality there were five, then the percentages would not sum up to 100%. In that case, it is simply necessary to add the three computed percentages $P_1$, $P_2$, $P_3$ which were obtained and subtract the sum of these three from 100%. This difference would be the percentage of the two remaining constituent gases and would include any errors which may be present. Solving Equations C-3, C-4, and C-5:

$P_1 = 0.790$ (methane)
$P_2 = 0.027$ (nitrogen)
$P_3 = 0.093$ (carbon dioxide)

The sum of these three portions is 0.910 (91%), but the sum of the constituents should be 1.0. Therefore, it may be assumed that there were some additional constituents in the gas sample and that their percentage is approximately 9%. These percentages represent the constituent gases in percent of the total volume.

Thus, far, the technique of adding heat to establish new conditions has been employed to then allow the establishment of three independent Equations, C-3, C-4, and C-5 in the example. If it were necessary to determine more constituent gas percentages, it would be necessary to write more equations.

Another method of establishing new operating conditions, whereby independent coefficients for writing additional equations similar to Equations C-3, C-4 and C-5 can be obtained, is to use several fluid oscillators with different lengths of feedback delay-line. In fact, there is nothing to preclude the combined use of adding heat to the sampled gas and having several lengths of feedback delay-line. This technique also gives additional readings on specific gravity and enhances the confidence factor on a specific gravity reading or observation.

For six different feedback delay-line lengths $l_1, l_2, \ldots l_6$, the following six equations can be written:

$$\sqrt{G} = \frac{L_1}{(prf)_1} \text{ for feed-back delay-line - } l_1$$

$$\sqrt{G} = \frac{L_2}{(prf)_2} \text{ for feed-back delay-line - } l_2$$

$$\sqrt{G} = \frac{L_2}{(prf)_2} \text{ for feed-back delay-line - } l_3$$

$$\sqrt{G} = \frac{L_2}{(prf)_2} \text{ for feed-back delay-line - } l_4$$

$$\sqrt{G} = \frac{L_2}{(prf)_2} \text{ for feed-back delay-line - } l_5$$

$$\sqrt{G} = \frac{L_6}{(prf)_6} \text{ for feed-back delay-line - } l_6$$

The values for $L_1, L_2, \ldots L_6$ are determined from experimental data and/or analytically. It has been found that, for a 10% change in feedback delay-line length, approximately 10% change in (prf) results.

From these six equations, six linear equations can be written for the determination of the constituent gas percentages, and also six independent determinations of the specific gravity "G" can be made. In determining the statistical value for G, each determination can be "weighted" because some values of G will be more favorable due to the feedback delay-line length and other instrumentation and implementation reasons.

Figure 9:
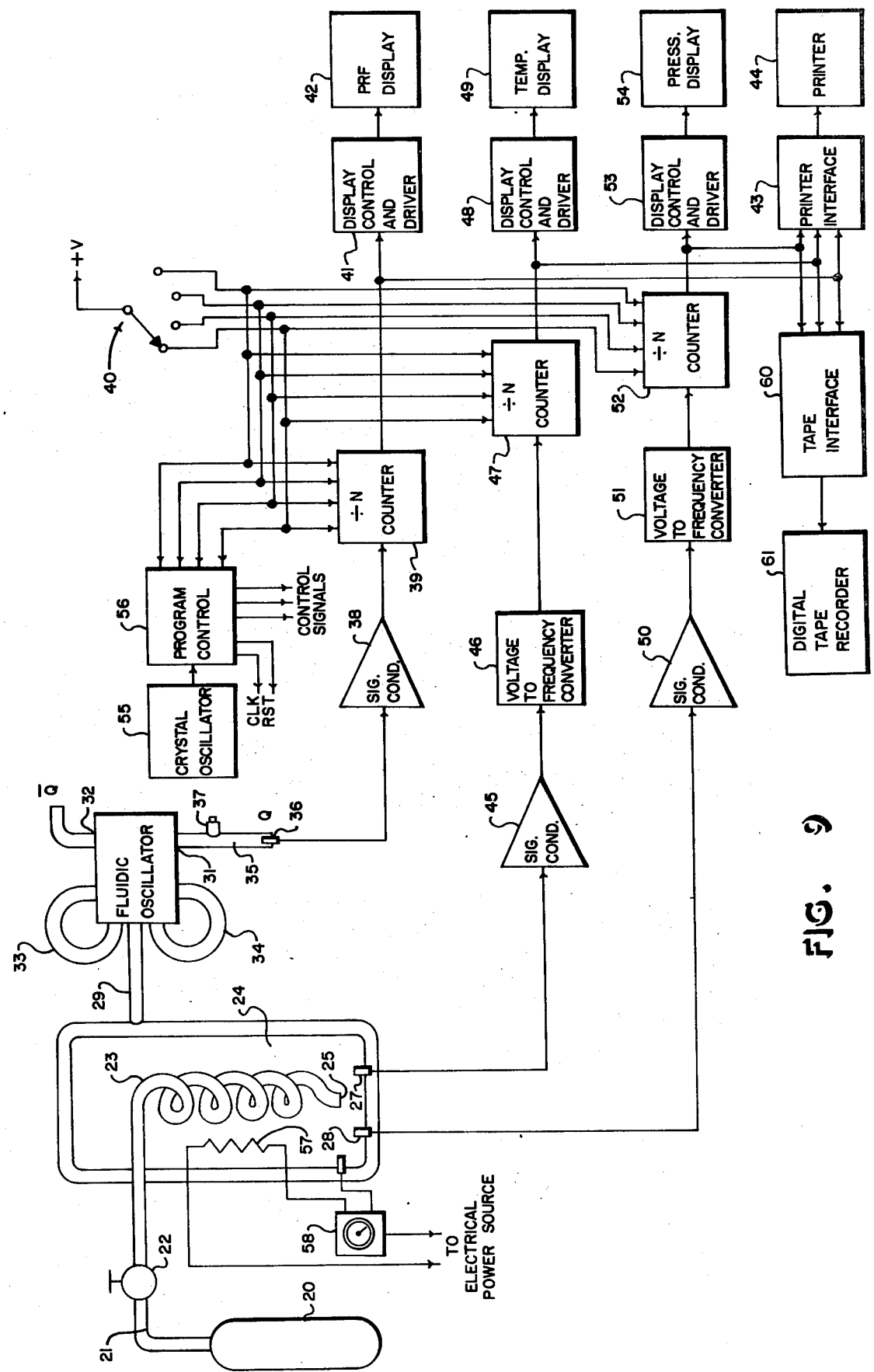
FIG. 9 is a simplified block diagram illustrating apparatus for obtaining the pulse repetition frequency of a fluidic oscillator obtained under measured temperature and pressure conditions.

FIG. 9 illustrates a presently preferred embodiment of apparatus for measuring and displaying the pulse repetition frequency of a fluidic oscillator along with the pressure and temperature of the supply fluid. A tank 20 containing gas under pressure is coupled through a line 21 and a pressure regulator 22 to a coil 23 disposed within the interior chamber of a surge tank 20, pressure regulated by the pressure regulator 22, fills the surge tank 24. The surge tank 24 is preferably surrounded by a layer of insulation 26 to assist in holding the sample gas at a predetermined temperature. A temperature transducer 27 and a pressure transducer 28 extend within the surge tank 26 to provide means for measuring the temperature and pressure of the sample gas as will be set forth more particularly below. The fluid enters chamber 24 through exit orifice 25. Orifice 25 is designed to induce thorough mixing of the fluid in chamber 24.

A line 29, in communication with the interior of the surge tank 24, permits the sample gas to flow from the interior of the surge tank 24 to the input port of an astable fluidic oscillator 30. The fluidic oscillator 30 is a two-stage device of which the second stage is a buffer having Q and $\overline{Q}$ outputs, 31 and 32, respectively. Feedback loops 33 and 34 obtain the astable multivibrator function in the manner previously described. The $\overline{Q}$ output from the fluid oscillator 30 is exhausted to the atmosphere. The Q output 31 is connected, via line 35, to a pressure transducer 36. It will be noted that the line 35 also has an exhaust port 37 to the atmosphere. The size of the exhaust port 37 is adjusted to obtain critically tuned pressure pulses within the line 35; i.e., substantially "square" waves without overshoot or undershoot. It is also important to likewise tune exhaust port $\overline{Q}$; the two exhaust ports must be balanced acoustically.

The output signal from the pressure transducer 36, a string of pulses at the repetition rate of the fluid oscillator 30, is applied to the input of a signal conditioner 38 which serve to further square-up the pulses for subsequent digital handling. From the signal conditioner 38, the pulses are applied to the input of a programmable counter 39.

Pulses are accumulated in the programmable counter 39 for a predetermined time span, typically two seconds to 80 seconds as selected by a manually operated switch 40. The division ratio of the programmable counter 39 is responsive to the position of the switch 40 such that the output is representative of the prf sensed during the preceding sample period. This output is applied to display control and driver 41 and is presented on a digital display 42. In addition, the output from the counter 39 is applied to a printer interface 43 which drives an optional thermal printer 44 to obtain a permanent record of the displayed quantity and to a tape interface 60 to permit recording on magnetic tape by the recorder 61 for subsequent processing of the data.

The signal from the temperature transducer 27 is applied to the input of a signal conditioning a d-c amplifier 45 which drives a voltage-to-frequency converter 46. Thus, the frequency of the output signal from the voltage-to-frequency converter 46 is proportional to the temperature of the gas within the storage tank 24 as sensed by the temperature transducer 27. This signal is applied to a programmable counter 47 whose division ratio is also controlled by the position of the switch 40. The parameters of the signal conditioner 45, the voltage-to-frequency converter 46, in conjunction with the characteristics of the temperature transducer 27, are adjusted such that the accumulated count within the programmable counter 47 at the end of a sample period directly represents the temperature within the surge tank 24. This count is applied to display control and driver 48 which drives digital display 49 for presenting the sensed temperature. In addition, the output from the programmable counter 47 is applied to the printer interface 43 to obtain a parallel record with the prf of the sensed temperature in the surge tank 24 and to the tape interface 60 to obtain, if desired, a digital record of the date.

Similarly, the output from the pressure transducer 28 is applied to the input of a signal conditioning d-c amplifier 50 which drives a voltage-to-frequency converter 51. The pulses issued by the voltage-to-frequency converter 51 are accumulated in a programmable counter 52 whose division ratio is controlled by the position of the manual switch 40. The parameters of the signal conditioner 50 and the voltage-to-frequency converter 51 are adjusted in accordance with the characteristics of the pressure transducer 28 such that the accumulated count in the programmable counter 52 at the end of a sample period directly represents the pressure within the surge tank 24. This quantity is applied to display driver 53 which drives digital display 54 to present a direct reading of the average pressure within the surge tank 24 during the sample period.

The accumulation and transfer of information throughout the apparatus is carried on synchronously under control of a crystal oscillator 55 and a program control counter 56 which issues clock, reset, and other control signals to the various modules. Program control counter 56 also receives sample period information according to the position of the manually operable switch 40 period.

The logic presented in FIG. 9 may employ integrated circuits of any suitable type. However, inasmuch as the present instrument is intended to be used in the field and hence battery operated, it is presently preferred that CMOS technology be employed in conjunction with liquid crystal displays. More particularly, in a specific embodiment of the invention, the signal conditioning amplifiers 38, 45, and 50 may be Texas Instruments type 082 operational amplifiers. The programmable counters 39, 47 and 52 may be type 4522 Divide-by-N Counters. The display control and driver 41, may comprise type 4534 Real-time Five-Decade Counters followed by type 4543 BCD-to-Seven Segment Latch/Decoder/Drivers for Liquid Crystals whereas the display control and drivers 48 and 53 may each comprise a type 4553 Three-Digit BCD Counter followed by type 4543 drivers. As previously mentioned, the digital displays 42, 49, and 54 are preferably, for power consumption purposes, of the widely available liquid crystal type. The voltage-to-frequency converters 46 and 51 may be type AD537 manufactured by Analog Devices, Inc. The pressure transducers 28 and 36 may each be of the bridge type as manufactured, for example, by Cognition, Inc. The temperature transducer 27 may be a type AD590 manufactured by Analog Devices, Inc. The printer interface 43 may comprise an array of 4042 Quad Latches. The crystal oscillator 55 and the program control counter 56 may comprise a type 4536 Programmable Timer. The fluidic oscillator 30 is preferably a General Electric type CR280 MV12 or equivalent. The tape interface 60 may comprise an array of 4042 latches, and the tape recorder 61 is preferably of the digital cassette type such as those manufactured by Memodyne, Inc.

As noted above in the dicussion of the method for determining the constituent gas percentages in a composite gas, the temperature of the gas may be changed to obtain additional equations. This may readily be accomplished by the heater 57 under control of the adjustable thermostat 58. In the system configuration of FIG. 9, the heater 57 may advantageously be wrapped about the coil 23 to preheat the sample gas before it is discharged into the surge tank 24.

It should not be construed, from the foregoing, that application of the invention is limited to the determination of natural gas characteristics. The principle is equally applicable, for example, to such applications as: monitoring the exhaust gases of an automobile to determine compliance with pollution control regulations; monitoring the stack gases of power plants and the like, etc. Additionally, the principle is applicable to the measurement of characteristics of liquids as well as gases.

Thus, while the principles of the inventions have now been made clear in an illustrative embodiment, there will be immediately obvious to those skilled in the art many modifications which are particularly adapted for specific environments and operating requirements without departing from those principles.

What is claimed is:

1. Apparatus for determining characteristics of a test gas comprising:
   (A) a fluidic astable oscillator having a supply port and alternative state output ports;
   (B) supply means for applying the test gas as the working fluid to said oscillator supply port, said supply means including:
      (i) a surge tank coupled between a source of the test gas and said oscillator supply port; and
      (ii) regulating means for regulating the pressure of the test gas applied to said oscillator supply port;
   (C) a first pressure transducer for electrically sensing pressure pulses at one of said output ports;
   (D) a second pressure transducer, said second pressure transducer being disposed in communication with the test gas in said surge tank;
   (E) a first voltage-to-frequency converter connected to receive the output signal from said second pressure transducer such that the frequency of pulses issued by said first voltage-to-frequency coverter is responsive to the pressure of the test gas within said surge tank;
   (F) timing means defining a predetermined time period;
   (G) first counter means for accumulating pulses from said first pressure transducer during said predetermined time period such that, at the end of said predetermined time period, the accumulated count is representative of the pulse repetition rate of said fluidic astable oscillator;
   (H) first record means for recording the pulse repetition rate at least temporarily;
   (I) second counter means for accumulating pulses from said first voltage-to-frequency converter during said predetermined time period such that, at the end of said predetermined time period, the accumulated count is representative of the pressure in said surge tank; and
   (J) second record means for recording the pressure of the test gas in said surge tank at leat temporarily.

2. The apparatus of claim 1 which further includes:
   (A) a temperature transducer disposed in communication with the test gas within said surge tank;
   (B) a second voltage-to-frequency converter connected to receive the output signal from said temperature transducer such that the frequency of pulses issued by said second voltage-to-frequency converter is responsive to the temperature of the test gas within said surge tank:
   (C) third counter means for accumulating pulses from said second voltage-to-frequency converter during said predetermined time period such that, at the end of said predetermined time period, the accumulated count is representative of the temperature in said surge tank; and
   (D) third record means for recording the temperature of the test gas and in said surge tank at least temporarily.

3. The apparatus of claim 2 in which said timing means includes means for selecting one of a plurality of selectable predetermined time periods.

4. The apparatus of claim 2 or 3 in which said first, second and third record means includes first, second and third digital displays for displaying, respectively, the pulse repetition frequency of said fluidic oscillator, the pressure of the test gas in said surge tank, and the temperature of the test gas in said surge tank.

5. The apparatus of claim 2 or 3 which further includes printer means coupled to said first, second and third counters for printing the pulse repetition frequency of said fluidic oscillator, the pressure of the test gas in said surge tank, and the temperature of the test gas in said surge tank.

6. The apparatus of claim 2 or 3 which further includes magnetic tape recording means coupled to said first, second, and third counters for digitally magnetically recording the pulse repetition frequency of said fluidic oscillator, the pressure of the test gas in said surge tank, and the temperature of the test gas in said surge tank.

* * * * *